US006300073B1

(12) United States Patent
Zhao et al.

(10) Patent No.: US 6,300,073 B1
(45) Date of Patent: *Oct. 9, 2001

(54) ONE STEP RT-PCR METHODS, ENZYME MIXES AND KITS FOR USE IN PRACTICING THE SAME

(75) Inventors: Ningyue Zhao, Milpitas; Helmut Wurst, Cupertino, both of CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/411,351

(22) Filed: Oct. 1, 1999

(51) Int. Cl.[7] ................................ C12Q 1/68; C12N 9/00
(52) U.S. Cl. .................... 435/6; 435/6; 435/183; 435/810
(58) Field of Search .................... 435/6, 91.1, 91.2, 435/183, 810; 536/23.1, 24.3, 24.33, 25.3

(56) References Cited

U.S. PATENT DOCUMENTS 6,048,734 * 4/2000 Burns et al. ..................... 436/180
6,130,045 * 10/2000 Wurst et al. ....................... 435/6

OTHER PUBLICATIONS

Mizutani et al., "Single–Step Reverse Transcription–Polymerase Chain Reaction for the Detection of Hepatitis C Virus RNA," Microbiol. Immunol., 42(8), 549–553, 1998.*
"Feature Chart for PCR Enzymes," Applied Biosystems (web site document), pp. 1 and 2, Jan. 2001.*
Mizutani et al., "Single–Step Reverse Transcriptase–Polymerase Chain Reaction for the Detection of Hepatitis C Virus RNA," Microbiology and Immunology, vol. 42, No. 8, pp. 549–553, 1988.*
Blain et al. (Nov. 1993), "Nuclease Activities of Moloney Murine Leukemia Virus Reverse Transcriptase," *Journal of Biological Chemistry*, vol. 268(31):23585–23592.
Blain et al. (Jul. 1995), "Effects on DNA Synthesis and Translocation Caused by Mutations in the RNase H Domain of Moloney Murine Leukemia Virus Reverse Transcriptase," *Journal of Virology*, vol. 69(7):4440–4452.

Sellner et al. (Feb. 1994), "Sensitive Detection of Ross River Virus—A One–Tube Nested RT–PCR," *Journal of Virological Methods*, vol. 49:47–58.
J.F. Burke, J. Wiley and Sons–New York, ed. (1996), "Series–VI Transcriptional Analysis Using PCR," Essential Techniques pp:61–63; 80–81.
Website: www.clontech.com, "AdvanTaq & AdvanTaq Plus PCR Kits User Manual, " pp. 1–19, Printed on Sep. 15, 1999.
Website: http://www.promega.com/tbs/tb220/tb220.html, "Access RT–PCR System and Access RT–PCR Introductory System," Revised Sep. 1998.
Website: http://www.lifetech.com/world_whatsnew/archive/nz_1_3.html, "SuperScript One–Step RT–PCR System," Printed on Sep. 21, 1999.

* cited by examiner

Primary Examiner—Bradley L. Sisson
(74) Attorney, Agent, or Firm—Bret E. Field; Bozicevic, Field & Francis

(57) ABSTRACT

Enzyme compositions, kits comprising the same and methods for their use in one-step RT-PCR are provided. The subject enzyme compositions at least include a mutant thermostable DNA polymerase and a mutant reverse transcriptase. In preferred embodiments, the mutant thermostable DNA polymerase is an N-terminal deletion mutant of Taq polymerase and the mutant reverse transcriptase is a point mutation mutant of MMLV-RT. The subject kits, in addition to the above described mutant thermostable DNA polymerase and mutant reverse transcriptase, at least include one of, and usually both of, dNTPs and a buffer composition, where the subject kits may further include additional reagents, including nucleic acids, a thermostabilizing agent, a glycine based osmolyte and the like. In practicing the subject methods, a reaction mix that at least includes template RNA, the above described mutant polymerase and reverse transcriptase, dNTPs, buffer, and nucleic acid primers is prepared. The resultant reaction mixture is maintained at a first set of reverse transcription conditions and then a second set of PCR conditions, whereby amplified amounts of DNA from a template RNA(s) are produced.

21 Claims, No Drawings

ONE STEP RT-PCR METHODS, ENZYME MIXES AND KITS FOR USE IN PRACTICING THE SAME

TECHNICAL FIELD

The field of this invention is nucleic acid amplification, and particularly one-step RT-PCR.

BACKGROUND OF THE INVENTION

Reverse transcription (RT) and the polymerase chain reaction (PCR) are critical to many molecular biology and related applications, particularly gene expression analysis applications. In these applications, reverse transcription is used to prepare template DNA from an initial RNA sample, e.g. mRNA, which template DNA is then amplified using PCR to produce a sufficient amount of amplified product for the application of interest. The RT and PCR steps of DNA amplification can be carried out as a two step or one step process.

In two step processes, the first step involves synthesis of first strand cDNA with a reverse transcriptase, e.g. MMLV-RT, following by a second PCR step. In certain protocols, these steps are carried out in separate reaction tubes. In these two tube protocols, following reverse transcription of the initial RNA template in the first tube, an aliquot of the resultant product is then placed into the second PCR tube and subjected to PCR amplification.

In a second type of two-step process, both RT and PCR are carried out in the same tube using a compatible RT and PCR buffer. In certain embodiments of single tube protocols, reverse transcription is carried out first, followed by addition of PCR reagents to the reaction tube and subsequent PCR.

In an effort to further expedite and simplify RT-PCR procedures, a variety of one step RT-PCR protocols have been developed. See e.g. the Relevant Literature section, supra. However, there is still room for improvement of these methods in a number of areas, including sensitivity, efficiency, and the like.

Accordingly, there is continued interest in the development of additional one step RT-PCR protocols, where a highly efficient and sensitive protocol is of particular interest.

Relevant Literature

See Blain & Goff, J. Biol. Chem. (1993) 5: 23585–23592; Blain & Goff, J. Virol. (1995) 69:4440–4452; Sellner et al., J. Virol. Method. (1994) 49:47–58; PCR, ESSENTIAL TECHNIQUES (ed. J. F. Burke, J. Wiley & Sons, New York)(1996) pp61–63; 80–81; SuperScript One-Step RT-PCR System description on the world-wide web at http://www.lifetech.com/world_whatsnew/archive/nz_1_3.html; Access RT-PCR System and Access RT-PCR Introductory System described on the world wide web at http://www.promega.com/tbs/tb220/tb220.html; and AdvanTaq & AdvanTaq Plus PCR kits and User Manual available at www.clontech.com at least as early as Sep. 15, 1999.

SUMMARY OF THE INVENTION

Enzyme compositions, kits comprising the same and methods for their use in one-step RT-PCR are provided. The subject enzyme compositions at least include a mutant thermostable DNA polymerase and a mutant reverse transcriptase. In preferred embodiments, the mutant thermostable DNA polymerase is an N-terminal deletion mutant of Taq polymerase and the mutant reverse transcriptase is a point mutation mutant of MMLV-RT. The subject kits, in addition to the above described mutant thermostable DNA polymerase and mutant reverse transcriptase, include at least one of, and usually both of dNTPs and a buffer composition, where the subject kits may further include additional reagents, including nucleic acids, a thermostabilizing agent, a glycine based osmolyte and the like. In practicing the subject methods, a reaction mix that at least includes template RNA, the above described mutant polymerase and reverse transcriptase, dNTPs, buffer, and nucleic acid primers is prepared. The resultant reaction mixture is then subjected to a first set of reverse transcription conditions and then a second set of PCR conditions, whereby amplified amounts of DNA from a template RNA(s).

DESCRIPTION OF THE SPECIFIC EMBODIMENTS

Enzyme compositions, kits comprising the same and methods for their use in one-step RT-PCR are provided. The subject enzyme compositions at least include a mutant thermostable DNA polymerase and a mutant reverse transcriptase. In preferred embodiments, the mutant thermostable DNA polymerase is an N-terminal deletion mutant of Taq polymerase and the mutant reverse transcriptase is a point mutation mutant of MMLV-RT. The subject kits, in addition to the above described mutant thermostable DNA polymerase and mutant reverse transcriptase, at least include one of, and usually both of, dNTPs and a buffer composition, where the subject kits may further include additional reagents, including nucleic acids, a thermostabilizing agent, a glycine based osmolyte and the like. In practicing the subject methods, a reaction mix that at least includes template RNA, the above described mutant polymerase and reverse transcriptase, dNTPs, buffer, and nucleic acid primers is prepared. The resultant reaction mixture is maintained at a first set of reverse transcription conditions and then a second set of PCR conditions, whereby amplified amounts of DNA from a template RNA are produced. In further describing the subject invention, the subject enzyme compositions will be described first, followed by a discussion of the subject kits and a review of the methods of amplifying a template RNA into DNA according to the subject invention.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Enzyme Compositions

As summarized above, the enzyme compositions of the subject invention are characterized by having at least one mutant thermostable polymerase and at least one mutant reverse transcriptase. Where the enzyme compositions include more than one thermostable polymerase, the number of different thermostable polymerases will generally be less than five, usually less than three and in many embodiments will be two. In such embodiments, the amounts of the two or more different polymerases are generally unequal. In addition, the amounts of the thermostable polymerase(s) and the reverse transcriptase(s) in the enzyme composition differ, where the ratio of polymerase to reverse transcriptase activity typically ranges from about 0.8 to 6.5, usually from about 1.6 to 6.5 and more usually from about 1.6 to 4.0 U polymerase/U RT, where 1 Unit of polymerase is defined as the amount of enzyme that will incorporate 10 nmoles of dNTPs into acid insoluble material per 30 minutes in a 10 minute incubation at 72° C. under the assay conditions and 1 Unit of RT is defined as the amount of enzyme that will incorporate 1 nmole of dTMP into acid insoluble material in 10 minutes at 37° C., with poly(A)/oligo(dT) as a substrate.

Thermostable Polymerase

The thermostable DNA polymerase of the enzyme compositions of the subject invention is characterized by having substantial polymerase activity, specifically DNA dependent DNA polymerase activity, but substantially no nuclease activity. Since the enzyme has substantial polymerase activity, it is capable of catalyzing the synthesis of DNA from deoxynucleotide triphosphates using a DNA strand as a template. Since the subject polymerase lacks nuclease activity, it is incapable of catalyzing the hydrolysis of the phosphodiester bonds of DNA polymers. By substantial polymerase activity is meant that the polymerase activity of the enzyme is at least about 80,000 units/mg protein. (Polymerase activity is determined by incubating 5 ml of diluted enzyme fractions with 5 µg of activated calf thymus DNA (Worthington, Freehold, N.J.) in a buffer containing 25 mM TAPS-KOH pH 9.3, 50 mM KCL, 5 mM $MgCl_2$, 1.4 mM β-mercaptoethanol, 200 µM each dNTP and $\alpha$-$^{32}$P dCTP (30–80 cpm/pmol) for 10 min at 72° C. in a total volume of 50 µl. The reaction is terminated by addition of 10 µl of 60 mM EDTA, and the products are precipitated by the addition of 60 µl of 20% trichloroacetic acid and incubation on ice for 15 min. The acid-insoluble product is then separated from the acid soluble nucleotides by filtration through GF/C filters. One unit represents conversion of 10 nmol of nucleotides in 30 min at 72° C.) By thermostable is meant that the enzyme maintains its polymerase activity at temperatures at least in excess of 55° C. and up to about 72° C. or higher. The thermostable polymerase is further characterized by having a higher $Mg^{2+}$ optimum as compared to wild type Taq polymerase (Barnes, W. M., Gene (1992) 112:29–35.

Generally, the thermostable polymerase has a molecular weight that is less than the molecular weight of naturally occurring or wild type *Thermus aquaticus* polymerase. The molecular weight of polymerases finding use in the subject compositions typically ranges from about 60 to 70 kDal, usually from about 62 to 68 kDal, and more usually from about 64 to 68 kDal, as measured by SDS-PAGE electrophoresis. The thermostable polymerase typically has an amino acid sequence in which the C-terminal portion is substantially identical to the carboxy domain of the naturally occurring *Thermus aquaticus* DNA polymerase as reported in Lawyer et al., J. Biol. Chem (1989) 264:6427 and having a Genbank accession no J04639, particularly amino acid residues 289 to 832 of the naturally occurring *Thermus aquaticus* DNA polymerase. By substantially identical or the same is meant that the C-terminal portion of subject enzyme, which is from about 530 to 550 amino acids in length, usually from about 540 to 550 amino acids in length and more usually 540 to 545 amino acids in length, where in many instances it is 543 amino acids in length, has an amino acid sequence that has a sequence identity of at least about 90%, usually at least about 95% and more usually at least about 99%, with residues 289 to 832 of the amino acid sequence of naturally occurring *Thermus aquaticus* polymerase, as measured using the BLAST algorithm, as described in Altschul et al., (1990) J. Mol. Biol. 215: 403–410 (using the published default settings). In many embodiments of the subject invention, the C-terminal 543 amino acid residues, e.g. 10 to 553, 17 to 560, etc, depending on the particular embodiment of the invention, of the polymerase are identical to residues 289 to 832 of wild type *Thermus aquaticus* polymerase. Where the amino acid sequence of the C-terminal domain of the polymerase does differ from residues 289 to 832 of the naturally occurring sequence, the difference is not one that significantly provides for a significantly reduced polymerase activity or specificity as compared that observed for the wild type enzyme, where any reduced polymerase activity will not exceed a 4-fold reduction, and usually will not exceed a 2 to 3 fold reduction.

Adjacent to the C-terminal domain described above is the N-terminal region of the enzyme. The N-terminal region at least comprises a sequence of nine amino acid residues that has less than 50% but at least 40% amino acid sequence identity with residues 280 to 288 of naturally occurring *Thermus aquaticus* polymerase, as measured using the BLAST algorithm described above, where the number of amino acid residues in the N-terminal domain that are identical with residues 280 to 288 is usually four. Generally, the sequence of this nine residue domain is:

$MRGHEX_1GLX_2$ (SEQ ID NO:1)

wherein $X_1$ and $X_2$ are hydrophilic residues, more specifically, polar uncharged hydrophilic residues. $X_1$ is usually either threonine or serine, and in many preferred embodiments is serine. $X_2$ is usually either asparagine or glutamine, and in many preferred embodiments is glutamine.

A preferred thermostable enzyme is further described in U.S. Pat. No. 6,130,045, the disclosure of which is herein incorporated by reference.

Reverse Transcriptase

Also present in the subject enzyme compositions is a mutant reverse transcriptase. The mutant reverse transcriptase is typically a mutant moloney murine leukemia virus reverse transcriptase (i.e. a mutant MMLV-RT), where the mutant preferably retains substantially all of the reverse transcriptase activity of the wild type MMLV-RT, where by substantially all is meant at least about 80%, usually at least about 90% and more usually at least about 95%, where in many embodiments the mutant reverse transcriptase retains about 100% of the wild type mmlv-rt reverse transcriptase activity, as determined by the activity assay disclosed in Blain & Goff, J. Biol. Chem. (1993) 268:23585–23592.

In many embodiments, the mutant reverse transcriptase is a point mutation mutant, in which a single residue of the wild type reverse transcriptase has been changed. Of particular interest in many embodiments is the R657S point mutant of MMLV-RT, where this particular enzyme is disclosed in Blain & Goff, J. Virol. (1995) 69:4440–4452 and Blain & Goff, J. Biol. Chem. (1993) 268:23585–23592.

Optional Components

In addition to the polymerase and reverse transcriptase components of the subject enzyme compositions, the subject enzyme compositions may also include a number of additional components.

One component of interest that is included in many preferred embodiments of the enzyme composition is a water-soluble temperature sensitive inhibitor of the thermostable DNA polymerase. Inhibitors of interest are those that bind to and inactivate the polymerase at temperature $T_1$ which is generally below about 85° C. For most practical purposes, $T_1$ is below about 55° C. Advantageously, however, the water-soluble temperature sensitive inhibitor dissociates from the DNA polymerase and becomes ineffective to inactivate the DNA polymerase at temperature $T_2$ which is generally above about 40° C. Preferably, $T_2$ is at least 5° C. above $T_1$. In many embodiments, $T_1$ is generally from about 40° C. to about 55° C. and $T_2$ is generally from about 75° to about 95° C. The inhibitor can be any biological or chemical molecule which will complex with the thermostable DNA polymerase to effect the noted temperature-dependent responses in the polymerase. Generally, the combined molecule (or complex) of DNA polymerase and temperature sensitive inhibitor is water-soluble. The inhibitor can be DNA polymerase-binding proteins which bind and release the DNA polymerase in response to temperature. Particularly useful inhibitors are antibodies (monoclonal or polyclonal) specific to the DNA polymerase which have the noted binding and releasing properties. The term "antibodies" includes the biological molecules one skilled in the art would normally understand that term to include, but in addition, it includes genetically prepared equivalents thereof, and chemically or genetically prepared fragments of antibodies (such as Fab fragments). The antibodies (and fragments thereof), can be used singly or in mixtures in the practice of this invention. Of particular interest in many embodiments are monoclonal antibodies. The monoclonal antibodies generally have an affinity for the thermostable DNA polymerase as defined by having an association constant of at least about $1 \times 10^7$ molar$^{-1}$. Preferably, the antibody is of either the IgG or IgM class. Most preferably, it is of the IgG class. Specific monoclonal antibodies of interest include the mouse monoclonal antibodies TP1, TP2, TP3, TP4, TP5, TP6, TP7, TP8, TP9, and TP14, where these and other inhibitors of interest are further disclosed in U.S. Pat. No. 5,338,671, the disclosure of which is herein incorporated by reference.

Other components that may be present in the enzyme composition include: proofreading enzymes, polymerase inhibitory oligonucleotides or analogues thereof, etc.

The enzyme composition may be present as a liquid (aqueous composition), where the composition may be frozen for storage stability. Storage stable compositions will typically comprise the enzyme in combination with a buffer medium. Buffer mediums of interest typically comprise: buffering agents, e.g. Tris, Tricine, HEPES, phosphate, etc.; solvents, e.g. water, glycerol, etc.; salts, e.g. KCl, NaCl, $(NH_4)_2SO_4$, etc.; reducing agents, e.g. β-mercaptoethanol, DTT, DTE, etc.; chelating agents, e.g. EDTA, CDTA, etc.; detergents, e.g. TRITON X100 (t-Octylphenoxypolyethoxyethanol), TWEEN 20 (polyoxyethylene(20) sorbitan monolaurate), THESIT (Polyethylene glycol 400 dodecyl ether), NP40 (Octylphenylpolyethylene glycol), etc.; and the like. Alternatively, the composition may be present as a substantially non-aqueous dried, storage stable composition, e.g. a freeze dried composition, to which water is added prior to use.

Kits

As summarized above, also provided are kits for use in preparing amplified amounts of DNA from a template RNA (s). The subject kits are characterized by at least including a mutant thermostable polymerase and a mutant reverse transcriptase, as described above, as well as at least one of dNTPs and a buffer composition (or the dried precursor reagents thereof, either prepared or present in its constituent components, where one or more of the components may be premixed or all of the components may be separate). In many embodiments, the subject kits will include both of these additional components, i.e. the kits will include the polymerase and reverse transcriptase enzymes, which may be present in a composition as described above or separate, as well as dNTPs and a buffer or components thereof.

By dNTPs is meant a mixture of deoxyribonucleoside triphosphates (dNTPs). Usually the kit will comprise four different types of dNTPs corresponding to the four naturally occurring bases, i. e. dATP, dTTP, dCTP and dGTP. The total amount of dNTPs present in the kit ranges, in many embodiments, from about 1.0 to 1000 μM, usually from about 1.0 to 500 μM and more usually from about 1.0 to 100 μM, where the relative amounts of each of the specific types of dNTPs may be the same or different. See e.g. U.S. Pat. No. 5,976,842, the disclosure of which is herein incorporated by reference.

The aqueous PCR buffer medium that is present in the subject kits includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 micro-ohms. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer is one that is elevated as compared to that employed in wild type Taq polymerase systems, and is one that is close to the optimum concentration for MMLV-RT, where the $Mg^{2+}$ concentration may range from 0.5 to 10 mM, but will preferably range from about 2 to 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5. Other agents which may be present in the buffer medium include chelating agents, such as EDTA, EGTA and the like and non-ionic detergents, such as TRITON X100 (t-Octylphenoxypolyethoxyethanol), TWEEN 20 (polyoxyethylene(20) sorbitan monolaurate), NP40 (Octylphenylpolyethylene glycol), and the like. As mentioned above, the aqueous buffer medium may be present in the subject kits as a fluid or frozen aqueous composition, as dried buffer precursors that may be separate or combined, e.g. as a freeze dried composition.

The subject kits may further include a number of optional components. Optional ingredients that may be present include: a thermostabilizing agent; a glycine based osmolyte, one or more nucleic acids, e.g. oligonucleotides, an RNase inhibitor, and the like. Each of these additional optional components is now described in greater detail.

The first optional component mentioned above is a thermostabilizing agent. The thermostabilizing agent should decrease the rate of denaturation of the reverse transcriptase to allow cDNA synthesis at elevated temperatures, where representative agents include: sugars, e.g. trehaloses, sucrose, raffinose, etc.; polymerase, e.g. PEG, Dextran, polysaccharides, etc.; and the like, where in many embodiments, trehalose is preferred. When included in the subject kits, the amount of thermostabilizing agent will typically range from about 0.9 to 15 mmol, usually from about 0.9 to 3.0 mmol and more usually from about 1.5 to 3.0 mmol.

Another optional component mentioned above is the glycine based osmolyte. Glycine-based osmolytes suitable for use in the present invention include trimethylglycine (BETAINE™), glycine, sarcosine and dimethylglycine. Glycine based osmolytes and their use in amplification reactions are further described in U.S. Pat. No. 5,545,539, the disclosure of which is herein incorporated by reference.

The kits may further include an RNase inhibitor. Suitable RNase inhibitors of interest include: human placental RNase inhibitor, recombinant RNase inhibitor, etc., where recombinant RNase inhibitor is of particular interest in many embodiments.

The kits may further include one or more nucleic acids, where the nucleic acids will generally be oligonucleotides that find use in the reverse transcription or amplification reactions, described in greater detail below. As such, nucleic acids that may be present include oligodTs, random primers and PCR primers. When present, the length of the dT primer will typically range from 12 to 30 nts. In certain embodiments, the oligo dT primer may be further modified to include an arbitrary anchor sequence, where the arbitrary anchor sequence or portion of the primer will typically range from 15 to 25 nt in length. Also present may be one or more sets of PCR primers, where such primers may be control primers etc. In certain embodiments, the primers may be a set of gene specific primers, as described in U.S. Pat. No. 5,994,076, the disclosure of which is herein incorporated by reference.

Other optional components that may be included in the subject kits include: one or more control sets of total RNA, e.g. mouse total RNA, water, and the like.

The various reagent components of the kits may be present in separated containers, or may all be (or in part be) precombined into a reagent mixture for combination with template DNA.

Finally, in many embodiments of the subject kits, the kits will further include instructions for practicing methods of producing amplified amounts of DNA from a template RNA(s), as described in greater detail below, where these instructions may be present on one or more of: a package insert, the packaging, reagent containers and the like.

Utility

The above described enzyme compositions and/or kits find use in methods of producing an amplified amount of DNA from a template RNA(s), i.e. producing one or more amplified amounts of DNA from one or more template RNAs. In particular, the above described enzyme compositions and/or kits find use in the one step RT-PCR reactions of the subject invention, as described in greater detail below.

In the subject one-step RT-PCR reactions, an amplified amount of DNA is produced from one or more, usually a plurality of, RNAs in a single reaction container without the sequential addition of reagents to the reaction container. Specifically, the one step RT-PCR methods of the subject invention include the following steps: (a) preparing a reaction mixture; (b) subjecting the prepared reaction mixture to a first set of reverse transcription reaction conditions; and (c) subjecting the reaction mixture to a second set of PCR conditions. Each of these steps is now described separately in greater detail.

The reaction mixture is prepared by combining at least the following components: (a) a mutant thermostable DNA polymerase, as described above; (b) a mutant reverse transcriptase, as described above; (c) one or more RNA templates; (d) dNTPs; (e) a quantity of reaction buffer; (f) reverse transcription primer, e.g. oligo dT; and (g) PCR primers. Other components that may be introduced into the prepared reaction mixture include: (a) a polymerase inhibitor; (b) a thermostabilizing reagent; (c) a glycine based osmolyte; (d) an RNase inhibitor; (e) control RNA and primers; and (f) water. The components are combined in a suitable container, e.g. a thin walled PCR reaction tube.

The following guidelines are based on the preparation of a 50 $\mu$l total volume reaction mixture. As such, the below specific amounts should be varied proportionally where different amounts of total reaction mixture are prepared, where such calculations are well within those of skill in the art. In preparing the reaction mixture, the amount of template RNA (e.g. total RNA) that is employed is typically at least about 10 pg, usually at least about 1 ng and more usually at least about 10 ng, where the amount of template RNA may be as great as 1 $\mu$g or greater, but typically does not exceed about 1 $\mu$g and usually does not exceed about 500 ng. As indicated above, the template RNA may be a single type of RNA, such that the template RNA is a homogenous sample, but is generally a heterogenous sample of two or more, usually at least about 50 or more and more usually at least about 100, 1000, or 5000 or more different RNAs (which differ from each other in terms of sequence). As such, the template RNA may be total RNA or mRNA, or a fraction thereof, derived from a physiological sample of interest.

The amount of mutant thermostable DNA polymerase that is included in the reaction mixture may vary, but typically ranges from about 5 to 30 U, usually from about 20 to 30 U. Likewise, while the amount of mutant reverse transcriptase may vary, the amount of this enzyme typically ranges from about 4 to 50 U, usually from about 5 to 15 U. In general, the total amount of these two enzymes included in the reaction mixture ranges from about 15 to 80 U, usually from about 25 to 45 U. The enzymes may be added to the reaction mixture separately or together as an enzyme composition, as described above.

Also included in the reaction mixture are dNTPs, i.e. an amount of each of dATP, dTTP, dCTP and dGTP. The total amount of dNTPs included in the reaction mixture ranges, in many embodiments, from about 20 to 80 nmols, usually from about 30 to 50 nmols and more usually from about 35 to 40 nmols, where the relative amounts of each of the specific types of dNTPs may be the same or different. See e.g. U.S. Pat. No. 5,976,842, the disclosure of which is herein incorporated by reference.

Also included in the reaction mixture is a quantity of reaction buffer, where suitable reaction buffers are described supra. The amount of reaction buffer used to prepare the subject reaction mixtures typically ranges from about 4 to 5.5 $\mu$l, usually from about 4.5 to 5.0 $\mu$l.

As mentioned above, the above amounts are provided for a 50 $\mu$l RT PCR reaction, and may be adjusted to any other reaction volume. Such adjustments are well within the abilities of those of skill in the art.

Also included in the reaction mixture is a reverse transcription primer, e.g. oligo dT, where such primers are described above. The amount of reverse transcription primer that is included typically ranges from about 10 to 30 pmol, usually from about 15 to 20 pmol. Random (e.g. hexameric) primers may also be included as primers for RT.

The reaction mixture also includes PCR primers. The oligonucleotide PCR primers from which the reaction mixture is prepared are of sufficient length to provide for hybridization to complementary template DNA under annealing conditions (described in greater detail below) but will be of insufficient length to form stable hybrids with non-complementary template DNA. The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers, depending on whether linear or exponential amplification of the template DNA is desired. Where a single primer is employed, the primer will typically be complementary to one of the 3' ends of the template DNA and when two primers are employed, the primers will typically be complementary to the two 3' ends of the double stranded template DNA.

As mentioned above, a number of additional optional components may be included in the reaction mixture. One such component is a polymerase inhibitor, e.g. an polymerase specific antibody, as described above. When present, the amount of the antibody typically ranges from about 0.2 to 2.2 $\mu$g, usually from about 0.9 to 1.1 $\mu$g. The reaction mixture may further include a thermostabilizing reagent, e.g. trehalose. When present, the amount of this reagent typically ranges from about 10 to 30 $\mu$mol, usually from about 20 to 30 $\mu$mol. Also present may be a glycine based osmolyte, e.g. betaine. When present, the mount of this reagent ranges from about 25 to 75 $\mu$mol, usually from about 40 to 50 $\mu$mol. Also present may be an RNase inhibitor, e.g. recombinant RNase inhibitor. When present, the amount of this reagent typically ranges from about 4 to 25 U, usually from about 10 to 20 U, where U is defined as 1 Unit of inhibitor being equal to the amount of protein required to inhibit the activity of 5 ng RNase A by 50%.

In preparing the reaction mixture, the various constituent components may be combined in many different orders. For example, the buffer may be combined with primer, polymerase and then template DNA, or all of the various constituent components may be combined at the same time to produce the reaction mixture. In many preferred embodiments, the enzymes are introduced into the reaction mixture last.

Following preparation of the reaction mixture, the reaction mixture is first subject to a set of conditions sufficient for reverse transcription of the RNA template present in the reaction mixture to occur, i.e. the reaction mixture is subjected to cDNA synthesis conditions. This first set of conditions is characterized by maintaining the reaction mixture at a substantially constant temperature for a period of time sufficient for cDNA synthesis to occur. The temperature at which the reaction mixture is maintained during this portion of the subject methods generally ranges from about 37 to 55, usually from about 45 to 52 and more usually from about 48 to 50° C. The duration of this step of the subject methods typically ranges from about 15 to 90 min, usually from about 30 to 60 min and more usually from about 50 to 60 min.

The next step of the subject methods is to subject the reaction mixture, which now includes cDNAs which are the result of the reverse transcription of the first step, to PCR conditions for a period of time sufficient for a desired amount of amplified DNA to be produced. The polymerase chain reaction (PCR) is well known in the art, being described in U.S. Pat. Nos.: 4,683,202; 4,683,195; 4,800,159; 4,965,188 and 5,512,462, the disclosures of which are herein incorporated by reference. In subjecting the cDNA comprising reaction mixture to PCR conditions during this step of the subject methods, the reaction mixture is subjected to a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98 and more usually from about 93 to 96° C. for a period of time ranging from about 3 to 120 sec, usually from about 5 to 60 sec.

Following denaturation, the reaction mixture will be subjected to conditions sufficient for primer annealing to template DNA present in the mixture. The temperature to which the reaction mixture is lowered to achieve these conditions will usually be chosen to provide optimal efficiency and specificity, and will generally range from about 50 to 75, usually from about 55 to 70° C. Annealing conditions will be maintained for a period of time ranging from about 15 sec to 60 sec.

Following annealing of primer to template DNA or during annealing of primer to template DNA, the reaction mixture will be subjected to conditions sufficient to provide for polymerization of nucleotides to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above steps of subjecting the reaction mixture to reverse transcription reaction conditions and PCR conditions be performed using an automated device, typically known as a thermal cycler. Thermal cyclers that may be employed for practicing the subject methods are described in U.S. Pat. Nos. 5,612,473; 5,602,756; 5,538,871; and 5,475,610, the disclosures of which are herein incorporated by reference.

The subject methods are characterized in that they are extremely efficient. As such, the subject methods can be used to prepare a large amount of amplified DNA from a small amount of template RNA. For example, the subject methods can be used to prepare from about 0.2 to 3.0, usually from about 0.8 to 1.5 $\mu$g amplified DNA from an initial amount of 1 ng to 1 $\mu$g, usually 100 ng to 500 ng of total RNA template in from about 25 to 40 cycles. The subject methods are also highly sensitive, being able to generate amplified DNA from exceedingly small amounts of template RNA, where by exceedingly small is meant less than about 1 $\mu$g, usually less than about 100 ng and more usually less than about 1 ng, where the methods generally require at least about 10 pg template RNA.

The subject one step RT-PCR methods find use in any application where the production of enzymatically produced primer extension product from template RNA is desired, such as the generation of libraries of cDNA from small amounts of mRNA, the generation of gene expression profiles of from or more distinct physiological samples, e.g. as required in gene expression analysis assays, and the like.

The following examples are offered by way of illustration and not by way of limitation.

EXPERIMENTAL

I. Protocol for Performing One Step RT-PCR

The following is a representative protocol for performing a one step RT-PCR reaction according to the subject methods.

1. Quickly thaw each tube in the kit and place on ice. Carry out all additions on ice.
2. Spin each tube briefly in a microcentrifuge and put back on ice.
3. In a sterile, RNAse free PCR thin wall tube, add the following reagents and mix well by pipetting up and down.

| | |
|---|---|
| X ul | RNAse free dH2O |
| 1 ul | 20 uM oligo dT |
| y ul | Total RNA (1 ug–1 ng) |
| 1 ul | 45 uM primers |
| 5 ul | 10 × One step RT-PCR buffer |
| 1 ul | 50 × dNTP |
| 0.5 ul | RNAse inhibitor (40 U/ul) |
| 25 ul | 1.2 M Trehalose |
| 10 ul | 5 M betaine |
| 1 ul | 50 × RT-PCR enzyme mix |
| 50 ul | Total volume |

4. Program the Thermocycler for the following:
   50° C. 1 hr, 1 cycle
   94° C. 5 min, 1 cycle
   94° C. 30 sec, 65° C. 30 sec, 68°0 C. 1–3 min*, 25–35 cycles
   68° C. 3 min, 1 cycle
   4° C. soaking
   *1–1.5 min/kb II. Efficiency of One Step RT-PCR of Subject Invention The protocol described in I above was used to amplify the following specific transcripts of varying abundance from an initial 1 μg of human placental total RNA.

| Lane | Transcript | Relative abundance | #PCR cycles |
|---|---|---|---|
| 1 | EGFR3 | low | 40 |
| 2 | p53 | low | 30 |
| 3 | IFN-8-R | med | 25 |
| 4 | ILGF-1 | low | 40 |
| 5 | PDGFB | low | 25 |
| 6 | IFN-8 | low | 30 |
| 7 | b-actin | high | 30 |
| 8 | IL-8 | low/med | 30 |
| 9 | G3PDH | high | 25 |

It was observed that the protocol of I above provided high yields of all fragments, regardless of initial transcript abundance.

III. Assay of Sensitivity of the Subject One Step RT-PCR

The target transcript was reverse transcribed at 50° C. for 1 hr and amplified using 40 PCR cycles, according to the protocol of I above. RT-PCR products were then analyzed via agarose/EtBr gel electrophoresis. In one experiment, serial 10-fold dilutions of a synthetic RNA (synthesized in vitro using T7 RNA polymerase) served as a template: $5\times10^5$ molecules of synthetic RNA; $5\times10^4$ molecules; $5\times10^3$ molecules; 500 molecules; 50 molecules; 5 molecules; 1 molecule; no template. Amplified product was clearly visible where only 50 template molecules were present. In a second experiment, different amounts of mouse liver total RNA were used as a template using the protocol of I above to amplify the β-actin transcript: 1 μg of total RNA; 100 ng; 10 ng; 1 ng; 100 pg; 10 pg; 1 pg; no template. Amplified product was detected from as little as 10 pg of total RNA template.

It is evident from the above results and discussion that novel enzyme compositions and reagent kits are provided, as well as novel methods for performing a one-step RT-PCR reaction mixture using these compositions and/or kits. Advantages of the subject invention over the prior art methods of RT-PCR include: ability to perform the entire RT-PCR reaction in a single container without the addition of additional reagents during the process, which feature reduces the possibility of contamination of the sample; greater efficiency as compared to other prior art methods of RT-PCR; high sensitivity; and the like. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An enzyme composition comprising:
   a mutant thermostable DNA polymerase lacking any nuclease activity, wherein the N-terminal domain of said DNA polymerase comprises a sequence of nine amino acid residues at least proximal to the N-terminus, wherein said nine amino acid residues are MRGHEX$_1$GLX$_2$, (SEQ ID NO:01) wherein X$_1$ and X$_2$ are hydrophilic residues selected from the group consisting of threonine, serine, asparagine and glutamine; and
   a mutant reverse transcriptase.

2. The enzyme composition according to claim 1, wherein said mutant DNA polymerase is a mutant Taq polymerase.

3. The enzyme composition according to claim 2, wherein said mutant Taq polymerase is a deletion mutant.

4. The enzyme composition according to claim 3, wherein said deletion mutant is an N-terminal deletion mutant.

5. The enzyme composition according to claim 1, wherein said mutant reverse transcriptase is a mutant of moloney murine leukemia virus reverse transcriptase.

6. The enzyme composition according to claim 5, wherein said mutant is a point mutation mutant.

7. The enzyme composition according to claim 6, wherein said mutant exhibits substantially the same RT activity as wild type moloney murine leukemia virus reverse transcriptase.

8. The enzyme composition according to claim 1, wherein said enzyme composition further comprises an antibody specific for said mutant thermostable DNA polymerase.

9. The enzyme composition according to claim 1, wherein said mutant thermostable DNA polymerase has a molecular weight ranging from about 60 to 70 kDal as measured by SDS-page.

10. An enzyme composition comprising:
   an N-terminal deletion mutant of Taq polymerase lacking any nuclease activity, wherein the N-terminal domain of said DNA polymerase comprises a sequence of nine amino acid residues at least proximal to the N-terminus, wherein said nine amino acid residues are MRGHEX$_1$GLX$_2$, (SEQ ID NO:01) wherein X$_1$ and X$_2$ are hydrophilic residues selected from the group consisting of threonine, serine, asparagine and glutamine;
   a point mutation mutant of moloney murine leukemia virus reverse transcriptase; and
   an antibody specific for said N-terminal deletion mutant of Taq polymerase.

11. The enzyme composition according to claim 10, wherein the ratio of said mutant Taq polymerase mutant to said reverse transcriptase mutant ranges from about 0.8 to 6.5.

12. The enzyme composition according to claim 10, wherein the amount of said antibody in said composition ranges from about 0.9 to 1.1 µg.

13. The enzyme composition according to claim 10, wherein said mutant thermostable DNA polymerase has a molecular weight ranging from about 60 to 70 kDal as measured by SDS-page.

14. A kit for use in a one step nucleic acid amplification procedure, said kit comprising:
   (a) a mutant thermostable DNA polymerase lacking any nuclease activity, wherein the N-terminal domain of said DNA polymerase comprises a sequence of nine amino acid residues at least proximal to the N-terminus, wherein said nine amino acid residues are MRGHEX$_1$GLX$_2$, (SEQ ID NO:01) wherein X$_1$ and X$_2$ are hydrophilic residues selected from the group consisting of threonine, serine, asparagine and glutamine;
   (b) a mutant reverse transcriptase; and
   (b) at least one of the following components:
      (i) dNTPs; and
      (ii) buffer.

15. The kit according to claim 14, wherein said kit further includes a thermostabilizing agent.

16. The kit according to claim 14, wherein said kit further includes a glycine based osmolyte.

17. The kit according to claim 14, wherein said kit further includes at least one nucleic acid.

18. The kit according to claim 14, wherein said kit further includes an RNase inhibitor.

19. The kit according to claim 14, wherein said mutant thermostable DNA polymerase has a molecular weight ranging from about 60 to 70 kDal as measured by SDS-page.

20. An enzyme composition comprising:
   a mutant thermostable DNA polymerase having a molecular weight ranging from about 60 to 70 kDal as measured by SDS-page, wherein the N-terminal domain of said DNA polymerase comprises a sequence of nine amino acid residues at least proximal to the N-terminus, wherein said nine amino acid residues are MRGHEX$_1$GLX$_2$ (SEQ ID NO:01)
   wherein X$_1$ and X$_2$ are hydrophilic residues selected from the group consisting of threonine, serine, asparagine and glutamine; and
   a mutant reverse transcriptase.

21. The enzyme composition according to claim 20, wherein said mutant DNA polymerase is a mutant Taq polymerase.

* * * * *